United States Patent [19]

Okajima

[11] Patent Number: 5,554,139
[45] Date of Patent: Sep. 10, 1996

[54] CATHETER

[75] Inventor: Naofumi Okajima, Tokyo, Japan

[73] Assignee: Terumo Kabushiki Kaisha, Tokyo, Japan

[21] Appl. No.: 364,297

[22] Filed: Dec. 27, 1994

[30] Foreign Application Priority Data

Dec. 24, 1993 [JP] Japan .................. 5-325610

[51] Int. Cl.$^6$ ............................. A61M 25/00
[52] U.S. Cl. .................. 604/282; 604/264; 128/656
[58] Field of Search ................. 604/282, 281, 604/280, 264; 128/656–658, 772

[56] References Cited

U.S. PATENT DOCUMENTS

| 4,636,346 | 1/1987 | Gold et al. | 264/139 |
| 4,739,768 | 4/1988 | Engelson | 128/658 |
| 5,178,158 | 1/1993 | De Toledo | 128/772 |

FOREIGN PATENT DOCUMENTS

| 87/07493 | 12/1987 | European Pat. Off. . |
| 0303487 | 2/1989 | European Pat. Off. . |
| 0386921 | 9/1990 | European Pat. Off. . |
| 0468133 | 1/1992 | European Pat. Off. . |
| 0523621 | 1/1993 | European Pat. Off. . |
| 0594201 | 4/1994 | European Pat. Off. . |
| 57-173065 | 10/1982 | Japan . |
| 60-500013 | 9/1985 | Japan . |
| 4-16676 | 4/1992 | Japan . |
| 4-44555 | 7/1992 | Japan . |

*Primary Examiner*—John D. Yasko
*Attorney, Agent, or Firm*—Burns, Doane, Swecker & Mathis, L.L.P.

[57] ABSTRACT

A catheter includes an inner layer, an outer layer, and an intermediate layer arranged between the inner and outer layers. This intermediate layer including a coil layer having a double layer coil portion composed of an inner coil wound in a first direction and an outer coil wound around the outside of the inner coil in a second direction that is opposite to the first direction, wherein the inner coil and the outer coil are formed from flat members whose ratios of thickness to width of cross section are less than 1. The intermediate layer further includes a rigid layer having a rigidity higher than at least one of the rigidities of the inner and outer layers. The rigid layer is arranged in a main body portion positioned in a proximal side of the catheter and the coil layer is arranged at least in a tip portion of the catheter which is positioned in a distal side of the catheter. The catheter further includes a distal end portion which has the largest flexibility among the portions of the catheter, and the intermediate layer is not arranged in the distal end portion. The distal end portion includes X-ray image forming element. The catheter further includes a hydrophilic lubricant layer provided around the inner layer and/or the outer layer.

27 Claims, 6 Drawing Sheets

CATHETER

BACKGROUND OF THE INVENTION

1. Field of the Invention

The present invention relates to a catheter, and in particular relates to a catheter used in medical surgeries carried inside blood vessels, selective injection of carcinostatic agents or angiography or the like.

2. Description of the Background Art

In recent years, it has become possible to replace certain medical surgical operations with medical surgeries that are carried directly inside blood vessels by inserting catheters into the blood vessels percutaneously to perform medical treatments to lesion parts of the blood vessels. In such inner-vessel medical surgeries, a catheter must be selectively inserted into a predetermined position in the narrow blood vessels which are meandered in complex and have many branches.

For example, when carrying out an inner-vessel medical surgery procedure so called as embolectomy which is to be performed to an aneurysm or arteriovenous tumor which sometimes appears in a blood vessel within the brain or the like, the tip of a small diameter catheter is selectively passed through a blood vessel of the brain until it reaches the lesion part or the vicinity thereof. Then, a liquid-type thrombus agent such as cyanoacrylate or solution of ethylene-vinylalcohol copolymer using dimethyl-sulfoxide as a solvent, a granulated-type thrombus agent such as polyvinylalcohol, or a thrombus member such as a tiny coil is brought to the tip of the catheter through a lumen thereof and then it is applied to or put on the lesion part from an opening formed on the tip or the lumen. When carrying out such procedures which involve the injection or application of a liquid-type thrombus agent, a medicine or a contrast agent into a narrow blood vessel, a narrow-diameter catheter must be selected and used in accordance with the purpose of the procedure.

Accordingly, these small-diameter catheters must have operability by which the catheter can be passed through a complex network of narrow blood vessels quickly and reliably in addition to chemical and biochemical safeness which are always required in commercially available catheters. Furthermore, in order to carry out injection of the thrombus agents as described above, the catheter is also required to have a sufficient chemical resistance, and in particular to have a sufficient solvent resistance which can prevent alternation from being caused in the catheter when the catheter contacts such solvents as dimethyl-sulfoxide (DMSO) or the like.

In more detail, the operability of the catheter described above includes the following characteristics or abilities. Namely, a catheter is required to have sufficient pushability and torque transmission ability. The pushability means the characteristics of the catheter that can reliably transmit a pushing force given by an operator at the base end of the catheter to the distal end thereof. The torque transmission ability means the characteristics that can reliably transmit rotational force applied to the base end of the catheter to the distal end thereof. Further, it is also required for a catheter to have follow-up characteristics and kink resistance characteristics. The follow-up characteristics mean the ability by which the catheter can advance smoothly within meandered blood vessel along a guide wire which has been in advance inserted into the blood vessel without causing injury to the blood vessel walls. The kink resistance characteristics mean the ability of the catheter that can prevent it from being bent by bent portions or curved portions of the blood vessel even after the catheter has reached the object position and the guide wire has been removed. Moreover, in order to effectively exhibit these characteristics, the outer surface of the catheter must possess lubrication characteristics.

These characteristics required to the catheter becomes difficult to obtain as the diameter of the catheter is reduced. As for the prior art for giving the pushability and the follow-up characteristics, there has been developed and proposed a catheter having a main body portion at the proximal side thereof which is formed into a double or two layer structure. The double layered structure is formed from a relatively rigid inner tube and a relatively flexible outer tube which covers the outer surface of the inner tube and has a portion that protrudes over the tip end of the inner tube.

One such example of the prior art catheter is disclosed in National Publication of the translation version of Utility Model No. 60-500013. The catheter is provided with an inner tube layer made of polyamide and an outer layer made of urethane, and the tip portion of the inner tube is formed into a tapered shape in such a manner that the inner diameter thereof is gradually increased. However, such a catheter has less solvent resistance since the outer tube layer is made of urethane, and this makes the catheter unsuitable for embolectomy use. Furthermore, in the prior art catheter, since there is a sudden change in rigidity at the boundary section between the portion comprised of the two tube layers of urethane and polyamide and the portion comprised of the single tube layer of urethane, the catheter is likely to be bent at that portion during operation. Namely, the catheter is likely to be bent or damaged due to the concentration of force at the boundary section between the two tube layers and the single tube layer. In particular, at the section in which only the single tube layer of urethane is arranged, stress is likely to be concentrated to the boundary section between the above two portions, because the single tube layer has fixed inner and outer diameters and has a uniform rigidity even at the tip portion thereof, which results in occurrence of kinks, Further, such structure makes it difficult for the catheter to follow the branches and bent portions within a blood vessel. That is to say, the prior art catheter has less follow-up characteristics.

Another example is shown in U.S. Pat. No. 4,636,346. The U.S. Patent discloses a guiding catheter which is comprised of a main section having a triple or three layer structure and a tip section having a double layer structure that extends from the tip of the main section. In this construction, the main portion has an intermediate layer having a relatively high rigidity provided between an inner layer and an outer layer. However, as the distal portion of the catheter is not provided with this intermediate layer, its torque transmission ability and kink resistance characteristics are not sufficient.

Yet another example is shown in Japanese Laid-Open Patent Publication No. 57-173065. This Laid-open publication discloses a catheter having a helically wound wire which is provided inside the catheter. This catheter is composed of a tube which extends along roughly the entire length of the catheter and a helically wound wire which terminates at the middle of the tube. However, in this catheter, since the helically wound wire is directly exposed inside the inner cavity of the catheter (lumen), there is the possibility that the lumen is clogged by a thrombus agent or a thrombus member. Further, there is also the possibility that a guide wire is caught by the helically wound wire when the guide wire is inserted. For these problems, it is required for an operator to operate the catheter carefully.

A further example is shown in U.S. Pat. No. 5,178,158. The U.S. Patent discloses a catheter having a single coil layer which is provided inside an intermediate layer made of polyimide and an outer layer made of polytetrafluoroethylene, in which the distal portion of the catheter is constituted so as to be more flexible than the proximal portion by making the pitch of the coil in the distal portion greater than the pitch of the coil in the proximal portion. However, in this catheter, since the single coil layer is formed of a coil wound in only one direction, the catheter has insufficient torque transmission and kink resistance characteristics. In particular, with regard to the torque transmission characteristics of the catheter, it depends on the rotational direction of the catheter. Namely, the torque transmission characteristics of the catheter are relatively good when the catheter is rotated in the direction that tightens the coil, but the torque transmission characteristics of the catheter are relatively poor when the catheter is rotated in the opposite direction, that is, the direction that loosens the coil. Accordingly, the catheter has limited torque transmission characteristics in one direction of rotation, and this results in poor operability for the catheter. Moreover, in the same manner as was explained in the preceding paragraph for the catheter disclosed in Japanese Laid-open Patent Publication No. 57-173065, because the coil is directly exposed inside the lumen, there is the possibility that the lumen is clogged by a thrombus agent and there is also the possibility that a guide wire is caught by the helically wound wire when the guide wire is inserted. Further, the sliding resistance of the guide wire is unavoidably increased. For these reasons, the operability of the catheter is not so good.

SUMMARY OF THE INVENTION

In view of the prior arts as described above, the main object of the present invention is to provide a catheter having excellent operability.

Another object of the present invention is to provide a catheter having excellent kink resistance characteristics.

Yet another object of the present invention is to provide a catheter having excellent torque transmission ability, that is a catheter which exhibits excellent torque transmission ability in spite of the rotational direction of the catheter.

Other object of the present invention is to provide a catheter having excellent follow-up characteristics which enable the catheter to surely follow a guide wire or bent portions of blood vessels.

Further object of the present invention is to provide a catheter having excellent pushability.

Further object of the present invention is to provide a catheter having excellent chemical resistance and solvent resistance property.

Further object of the present invention is to provide a catheter which is suitable for use in medical treatments for blood vessels in the brain.

Yet further object of the present invention is to provide a catheter instrument provided with such a catheter as described above, and in particular to provide such a catheter which is suitable for use in medical treatments for blood vessels in the brain.

In order to achieve these objects, a catheter according to the present invention comprises an inner layer; an outer layer; and an intermediate layer arranged between the inner and outer layers, the intermediate layer including a coil layer having a double layer coil portion composed of an inner coil wound in a first direction and an outer coil wound around the outside of the inner coil in a second direction that is opposite to the first direction, wherein said inner coil and said outer coil are formed from flat members whose ratios of thickness to width of cross section are less than 1.

In the present invention, it is preferred that the intermediate layer further includes a rigid layer having a rigidity higher than at least one of the rigidities of the inner and outer layers.

Further, it is also preferred that the catheter has a main body portion is positioned at a proximal side of the catheter in an axial direction thereof and a tip portion at a distal side of the main body portion, in which the rigid layer is arranged in the main body portion and the coil layer is arranged at least in the tip portion.

Further, it is also preferred that the rigid layer is arranged such that at least a part of the rigid layer overlaps the coil layer. In this case, preferably, the rigid layer has a rigidity reducing means for reducing the rigidity of the rigid layer at a tip side of the rigid layer.

Furthermore, it is preferred that the coil layer has a first portion having a relatively high rigidity and a second portion having a rigidity less than that of the first portion, and the second portion is positioned at the distal side of the catheter than the position of the first portion.

Moreover, it is also preferred that the double coil layer portion has a tip end, and the coil layer further includes a single coil layer coupled to the tip end of the double layer coil portion, and the single coil layer is formed from either of the inner or outer coil. In this case, preferably, the rigidity of the inner coil is different from that of the outer coil.

Moreover, it is also preferred that the coil layer is arranged over a substantially entire length of the catheter. In this case, the inner layer is preferably arranged over a substantially entire length of the catheter.

Further, it is preferred that the inner layer has a constant inner diameter along the entire length of the catheter, and the inner layer has an inner surface which defines a lumen and the inner surface is formed into a smooth surface having no step portion. In this case, the inner surface of the inner layer is formed so as to have a low frictional characteristic and the inner surface has a chemical resistance property. As for the materials for constructing the inner layer, at least one material selected from the group consisting of soft fluorine-based resin, low density polyethylene and denaturated polyolefine is adopted.

Furthermore, it is also preferred that the outer layer is formed from a heat shrinkable resin which is shrunk when heated.

Moreover, it is also preferred that the outer layer includes at the proximal side of the catheter a first region which is relatively rigid, and at the distal side from the first region a second region which is relatively flexible.

Further, it is preferred that the outer layer has a coupling section disposed between the first and second regions for coupling these regions, and the coupling section has a rigidity between the rigidities of the first and second regions.

Furthermore, it is also preferred that the catheter further comprises a hydrophilic lubricant layer provided around the inner layer and/or the outer layer. In this case, it is also preferred that the hydrophilic lubricant layer has anti-thrombogenic characteristics.

Moreover, it is also preferred that the catheter further includes a distal end portion which has the largest flexibility among the portions of the catheter, and the intermediate layer is not arranged in the distal end portion. In this case, preferably, the distal end portion includes X-ray image forming element.

Furthermore, it is preferred that the catheter be adapted for insertion into cerebral blood vessels. In this case, the outer diameter of the catheter is preferably less than or equal to 1.0 mm, and the outer diameter of the portion is preferably less than or equal to 0.8 mm.

Another aspect of the present invention is directed to a catheter instrument, which comprises: a catheter including an inner layer; an outer layer; and an intermediate layer arranged between the inner and outer layers, the intermediate layer including a coil layer having a double layer coil portion composed of an inner coil wound in a first direction and an outer coil wound around the outside of the inner coil in a second direction that is opposite to the first direction, wherein said inner coil and said outer coil are formed from flat members whose ratios of thickness to width of cross section are less than 1; and a guide wire which is used by being inserted into a lumen defined by the inner layer of the catheter.

In this case, it is preferred that the guide wire is composed of a core member, an X-ray image forming element provided at a tip portion of the core member, and a coating layer which covers the outer surface of the core member. Alternatively, it is also possible to constitute the guide wire from a core member, a coating layer which covers the outer surface of the core member and a hydrophilic lubricant layer fixed onto the outer surface of the coating layer.

Another aspect of the present invention is directed to a catheter instrument, which comprises: a catheter including an inner layer; an outer layer; an intermediate layer arranged between the inner and outer layers, the intermediate layer including a coil layer having a double layer coil portion composed of an inner coil and an outer coil, wherein said inner coil and said outer coil are formed from flat members whose ratios of thickness to width of cross section are less than 1; and a guiding catheter having a lumen through which the catheter is inserted.

In this case, it is preferred that the guiding catheter has inner and outer surfaces, and a hydrophilic lubricant layer is arranged onto the inner and/or outer surface.

DESCRIPTION OF THE INVENTION

Hereinbelow, the structure of the catheter according to the present invention will be explained in more detail.

In particular, the catheter of the present invention is formed so as to have a relatively small diameter. Namely, it is preferred that the outer diameter of the catheter be less than or equal to 1.0 mm, and it is further preferred that the outer diameter of the tip portion of the catheter be less than or equal to 0.8 mm. In this way, the catheter of the present invention will be preferably adapted for insertion into cerebral blood vessels.

The relatively flexible inner layer is formed of a synthetic resin tube. It is preferred that the inner layer extends over the substantially entire length of the catheter, but it is possible to connect a separate member in the middle of the inner layer. For example, in a case where the tip portion of the catheter is required to have more flexibility, an inner layer at the tip portion can be formed of more flexible material, and thus formed inner layer can be connected to the inner layer on the main body portion. Further, it is also possible to employ a tube-shaped member as the inner layer, in which the tube-shaped member is formed by extrusion molding in accordance with following process. Namely, a portion of the tube-shaped member corresponding to the main body portion is first formed by extrusion molding using a relatively rigid material, a next portion of the tube-shaped member corresponding to the boundary section between the main body portion and the tip portion is then formed by extrusion molding using the relatively rigid material into which a relatively flexible material is gradually being added to decrease its rigidity, and a portion of of the tube-shaped member corresponding to the tip portion of the catheter is finally formed by extrusion molding using only the relatively flexible material. Specifically, this tube-shaped inner layer is formed from the integrally formed tube-shaped member including a main body portion which is formed of the rigid material, a tip portion which is formed of the flexible material, and a boundary portion which is positioned between the main body portion and the tip portion and which is formed of the material in which the ratio of the flexible material contained therein increases toward the tip direction while the ratio of the rigid material contained therein decreases.

The inside of the above described inner layer constitutes a lumen which is a longitudinal space through which guide wires, medicines, thrombus agents or the like can be passed. In this case, it is preferred that the diameter of the lumen, that is the inner diameter of the inner layer is constant from the main body portion to the tip portion. However, the inner diameter of the inner layer at the tip portion can be reduced toward the distal end of the catheter. In this case, the outer diameter of the outer layer at the tip portion is also reduced toward the distal end. Further, the thickness of the inner layer at the tip portion may be the same as that of the inner layer at the main body portion. However, it is preferred that the thickness of the inner layer at the tip portion is thinner than that of the main body portion, because such construction improves flexibility of the catheter.

It is preferred for the materials for constructing the inner layer to have excellent chemical resistance characteristics so as not to receive any inverse effects from medicines which are passed therethrough, in particular, as for the catheter for use in embolectomy, it is preferred that the materials for constructing the catheter have solvent resistance characteristics since there are cases that the thrombus agents contain solvents such as DMSO, ethanol, or cyanoaclylate or the like.

Further, in order to improve slidability when guide wires as described later are passed through the lumen or in order to make passage of a thrombus member such as a tiny coil easy, it is preferred that the inner layer is formed of the materials which can impart good slidability and provide smooth inner surface. For this reason, materials which can satisfy flexibility, chemical resistance characteristics and slidability are preferably used. For example, soft fluoroethylene resin such as fluorine-contained elastomer or the like, linear low density polyethylen (LLDPE) and denaturated polyolefine can be used as the materials. Further, it is also preferred that hydrophilic treatment is applied onto the inner surface of the inner layer in order to improve the slidability further. This hydrophilic treatment can be made by the method that forms hydrophilic lubrication layer described later or the method that water swilling compound is fixed to the inner layer directly or by means of binders.

The above described intermediate layer provided in the main body portion is composed of a rigid layer and a coil layer, and the intermediate layer provided in the tip portion is formed of a coil layer. In another example of the intermediate layer, it is formed from a rigid layer provided in the main body portion of the catheter and a coil layer which is provided so as to extend from the tip end of the rigid layer over the tip portion off the catheter. Further, in the other example for the intermediate layer, it is formed from a coil layer provided over the main body portion and the tip portion, in which a portion of the coil layer provided in the main body portion is formed from a double coil layer comprised of two coils wound in opposite directions to each other.

The intermediate layer is provided around the outside of the inner layer as well as inside the outer layer described later. Either one of the coil layer and the rigid layer may be provided inside the other layer. The intermediate layer is not necessarily bonded to the inner layer and the outer layer if the torque transmission ability and the pushability of the catheter is practically useful. However, if at least the tip end and the base end of the intermediate layer are bonded to these layers, the torque transmission ability and the pushability of the catheter is improved.

The rigid layer described above has relatively high rigidity, and it is provided in order to improve rigidities in the axial direction, circumferential direction and radial direction of the catheter and improve the pushability that is the ability for transmitting pushing force added at the base end of the catheter to the tip end thereof. In this regard, it should be noted that in a case where the inner and outer layers have a fairly high rigidity or in a case where the rigidity of the coil layer is sufficient for the required rigidity, it is possible to omit the provision of the rigid layer. The thickness of the rigid layer is set so as to be constant along the axial direction of the catheter. However, it is possible to construct the rigid layer such that the thickness thereof at the tip portion of the catheter is gradually reduced toward the distal end thereof. Further, it is also possible to form a spiral-shaped slit on or near the tip end of the rigid layer. The pitch of the spiral-shaped slit may be a constant size. However, it is preferable to change the pitch continuously or in a stepwise manner toward the the tip end of the rigid layer. Furthermore, at the tip end of the rigid layer, it is possible to form a plurality of slits which extend in the axial direction. These slits may be formed so as to cut the rigid layer or not.

As for the material for constructing the rigid layer, it is not limited to a specific material even if it can improve the rigidities in the axial direction, circumferential direction and radial direction of the catheter and can have the pushability that is the ability for transmitting pushing force added at the base end of the catheter to the tip end thereof. In a case where plastic materials are used, preferable example includes polyimide or liquid-crystal polymer or the like. Further, the rigid layer may be formed into a metal layer formed from a pipe or mesh of stainless steel (SUS304) or a metallic braid. Furthermore, a braid which covers the outer surface of the coil layer so as to restrict possible deformation of the coil can be used as the rigid layer.

The coil layer described above is provided in order to impart excellent torque transmission ability and anti-kinking characteristics, which in turn further improves the pushability. The coil layer is provided so as to extend at least from the tip end of the rigid layer to the distal end of the catheter. It is of course possible to arrange such a coil layer so as to extend roughly the entire length of the catheter. By providing the coil layer from the tip end of the rigid layer (a portion where the rigid layer terminates) to the distal side thereof as described above, the difference in rigidity which is caused by presence or not presence of the rigid layer can be moderated, thereby enabling to prevent kink from being caused. Further, it is also possible to reduce the thickness of the rigid layer at the tip end thereof. In this way, the anti-kinking characteristics are further improved. In this case, it is preferred that the coil layer terminates before the distal end portion of the catheter. As a result, the distal end portion becomes the most flexible portion in the catheter.

The coil layer includes a double layer coil portion which is composed of an inner coil and an outer coil which are wound in opposite directions. A single layer coil can be coupled to the double layer coil portion. Further, it is also possible to use a triple layer coil which is formed by winding a single layer coil onto the double layer coil.

Each coil which form the respective coil portion is preferably formed from flat members whose ratios of thickness to width of cross section are less than 1. In this case, examples of the flat members include a flat coil wire, a flat tape and a flat ribbon. Further, the flat members can be formed from a flat filamentous member formed by cutting out a pipe shaped member helically, for instance. The cross section of the flat members are not limited to a quadrilateral shape or a rectangular shape. It is possible to form the cross section of the flat members so as to have a long ellipse shape or any other four-cornered shape, this way, it is possible to construct a catheter having an outer diameter of less than or equal to 1.0 mm, which makes it possible to achieve the results described previously above.

Winding pitch of the coil positioned at the main body portion of the catheter may be the same as that of the coil positioned at the tip portion of the catheter. However, it is of course possible to change the pitch at a part of the coil in order to change the distribution of the rigidity of the coil. In this regard, it should be noted that the pitch means the distance including the width of the flat member which forms the coil (in a case where the flat member is formed into a flat coil wire which has a cross section of rectangular shape, the width of the coil means the length of the longitudinal edge thereof) and the spacing between two adjacent windings of the coil wire. For example, if the coil spacing of a coil positioned in the main body portion is smaller than that of a coil positioned in the tip portion, if the width of a coil positioned in the main body portion is larger than that of a coil positioned in the tip portion, or if the thickness of a coil positioned in the main body portion is larger than that of a coil positioned in the tip portion, it becomes possible to improve the rigidity of the main body portion of the catheter rather than that of the tip portion thereof. Further, if the coil pitch is changed so as to be larger, the width of the coil is changed so as to be smaller or the thickness of the coil is changed so as to be thinner in the region which extends from the tip end of the rigid layer where the rigid layer terminates toward the distal end of the catheter, it becomes possible to change flexibility of the main body portion and the tip portion of the catheter in a stepwise manner including three step portions or four step portions, or continuously (in no stepwise manner).

Further, in the double layer coil portion, it is possible to construct it so that the flexibility or the inner coil is different from that of the outer coil. As the means for changing the flexibility, for example, the thicknesses of the coils or the construction materials of the coils may be changed. Further, it is also possible to change the cross-sectional shapes or the coil pitches of these coils. Furthermore, any combination of these methods can be adopted. In this case, the coil layer may be formed into a structure in which the coil layer positioned in the main body portion is constructed from the double layer coil and the coil layer positioned in the tip portion is constructed such that either one of the inner and outer coil terminates in the middle of the other coil. According to this structure, the flexibility of the catheter can be changed in a multiple stepwise manner along its axial direction. As for the coil used in the coil layer, a metallic coil formed from a stainless steel (SUS304) or super elastic alloy or a plastic coil formed of a polyethylenetelephsalate, polyimide, polyamide, or polycarbonate or the like are preferably used.

The outer layer described above is formed from a relatively flexible tube-shaped member. Further, the outer layer may be formed from a coating of flexible materials applied onto the outer surface of the inner layer or the intermediate layer. Furthermore, the outer layer may be formed from a tube which is composed of a main body portion formed of a relatively high rigidity synthetic resin, a tip portion formed of a relatively low rigidity synthetic resin and a connection portion (transition part) which is formed by changing the ratio (for example, mixing ratio) of the contained high rigidity synthetic resin and low rigidity synthetic resin along the axial direction thereof continuously or in a stepwise manner and which is formed with the main body portion and the tip portion, respectively. Moreover, the outer layer may be formed by coupling a high rigidity tube to a low rigidity tube with another tube having intermediate rigidity. Moreover, the outer layer may be formed by joining a high rigidly tube with a low rigidity tube in such a manner that they overlap to the extent of 1 mm to 20 mm. In this case, it is preferred that these tubes are overlapped and joined such that the tip side of the high rigidity tube corresponding to the main body portion gradually decreases its thickness toward the distal side, while the low rigidity tube corresponding to the tip portion gradually increase its thickness, since according to this joining method the distribution of the rigidity becomes smooth and it is possible to have a large joining area between these tubes.

The outer layer can be for example formed by putting a heat shrinkable tube which is made of polyolefine resin such as polyethylene or polypropylene or the like onto the outer surface of the inner layer or the intermediate layer and then applying heat to cause the tube heat-shrunk. Further, it is also preferred that the outer layer is formed from materials having good compatibility for living body, and in particular materials having good anti-thrombogenic characteristics.

Further, it is also preferred that a hydrophilic lubrication layer is formed on the outer surface of the outer layer. The hydrophilic lubrication layer is preferably formed of materials which will exhibit lubrication characteristics when water is added. The hydrophilic lubrication layer may be simply coated onto the outer layer. However, it is preferred that the hydrophilic lubrication layer is fixedly adhered onto the outer surface of the outer layer under the bonding force practically used. It is also preferred that another treatment which will be able to exhibit higher compatibility for living body when used is made onto the outer surface of the outer layer. As for the compatibility for living body, it is required to have anti-thrombogenic characteristics. In a preferred example, anti-thrombogenic agents are applied onto the outer surface by using a coating of heparin solution or a heparin bonding. In this case, it is more preferable that such heparin is fixed onto the outer surface of the outer layer. Further, it is possible to form the outer layer by mixing thrombus solution into the construction materials of the outer layer and then conducing extrusion molding to produce a tube-shaped member. If such a tube-shaped member is used as the outer layer, it is preferred that the thrombus solution is gradually released from the outer layer when it contacts with blood or the like when used.

It is preferred that a block-copolymer formed by a hydrophilic compound block and a hydrophobic compound block is fixed onto the outer surface of the outer layer as the hydrophilic lubrication layer, since lubrication characteristics as well as anti-thrombogenic characteristics are both improved. The materials are preferably formed from water-swelling compounds. Example of such copolymer includes a block-copolymer of polyglycidyl-methacrylate (PGMA) and dimethyl-acrylicamide (DMAA).

Moreover, it is also preferred that there is formed the most flexible distal end portion at the distal side of the tip portion of the catheter. The distal end portion of the catheter is preferably formed from a double layer coil composed of the outer layer and the inner layer. Furthermore, the distal end portion can be formed from one of the outer and inner layers. Moreover, the distal end portion can be formed by fixedly attaching a separate flexible member by fusion or bonding. Further, it is preferable for the distal end portion to have a narrow diameter portion in which the outer diameter decreases toward the distal end of the catheter or a constricted portion in which the outer diameter is partially reduced. By providing thus formed distal end portion, the follow-up ability for blood vessels or guide wires are further improved, and the effectiveness which prevents blood vessels from being injured when the catheter is inserted into the blood vessels is also remarkably improved, thereby enabling to safely insert the catheter into blood vessels such as blood vessels in the brain which are narrow and are likely to be damaged. Further, it is also preferable to provide an X-ray image forming element on the distal end portion. The X-ray image forming element is mounted by a coil-shaped or a ring-shaped wire formed of a material such as gold, white gold or tungsten or the like is wound around or embedded into the distal end portion. In this way, it becomes possible to confirm the position of the distal end portion within the living body under the X-ray inspection.

Furthermore, it is also possible to provide another means for preventing abrupt change from being caused in the rigidity of the catheter at the region extending from the tip end of the rigid layer to the distal side thereof. Namely, it is possible to provide a kinking preventing tube at a desired position, thereby enabling to prevent kinking from being caused.

According to the catheter of the present invention as described above, it is possible to obtain excellent pushability due to the presence of the intermediate layer and improve the torque transmission ability and anti-kinking characteristics due to the presence of the coil layer. In particular, since the coil layer has the double layer coil portion in which two coils are wound in opposite directions, excellent torque transmission ability is realized irrespective of the rotational direction thereof when rotation is added to the catheter at the base end thereof. Further, in the tip portion, pushing force and torque imparted from the main body portion are surely transmitted to the tip portion due to the presence of the coil layer disposed between the inner and outer layers and extending from the main body portion. Further, the catheter is provided with the anti-kinking characteristics as well as the flexibility, good follow-up ability for blood vessels and guide wires can be exhibited. Furthermore, since the inner layer is provided so as to extend over the entire length of the catheter, that is it is provided continuously from the main body portion to the tip portion of the catheter, things which pass through the lumen, that is guide wires or like will not be caught inside the catheter. Further, since the inner surface of the lumen is formed into smooth surface having low frictional resistance, it is possible to insert the catheter smoothly along the guide wire. Moreover, the functions and the advantages described above can be obtained, even if the outer diameter of the catheter is small such as a catheter constructed for use in treatments for blood vessels in the brain.

The above described catheter according to the present invention can be used with a guide wire. In this case, a combination of the catheter and the guide wire constitutes a catheter instrument. The guide wire is formed from a metallic core, an X-ray image forming coil and a coating layer coated onto the outer surface of the core, and thus formed guide wire is preferably used. In this case, the coating layer is preferably formed of fluorine-contained resin. As the other preferred example of the guide wire, it is formed from a core, a coating layer of plastic which is coated onto the outer surface of the core, and a hydrophilic lubrication layer fixedly applied onto the outer surface of the coating layer.

In the guiding catheter, there is formed with a lumen through which the above described catheter, in particular a catheter used for treatment for blood vessels in the brain can be inserted. As for the materials for constructing the guiding catheter, polyvinyl chloride. polyethylene, polypropylene, polyurethan elastomer, polyamide elastomer, or polymer polymer-alloy containing polyamide therein or the like is preferably used. In this case, it is possible to provide a hydrophilic lubrication layer onto the outer surface or inner surface of the guiding catheter in the same manner as described above.

Hereinbelow, explanation will be made with reference to the example of the operations of the catheter according to the present invention, in which the catheter is used in embolectomy for cerebral aneurysm.

First, the guiding catheter having a lumen through which the catheter of the present invention can be inserted is prepared. Next, the guiding catheter is inserted from femoral artery into arteria carotis interna, arteria carotis external or vertebral artery through aorta, and thus inserted catheter is put there in this case, it should be noted that the inner and outer surfaces of the catheter is covered by a hydrophilic lubrication layer.

Next, a guide wire is put in the lumen of the catheter according to the present invention. The catheter is inserted into the lumen of the guiding catheter by operating its end portion. After the distal end of the catheter is protruded from the opening formed at the tip end of the guiding catheter, the catheter according to the present invention and guide wire are moved forward so as to be inserted into the blood vessels to be treated. In this case, the catheter is provided with the intermediate layer having a coil layer, the pushing force added at the base end can be transmitted to the distal end of the catheter reliably.

When the catheter reaches at a branch portion of blood vessels under the above described processes, the guide wire is directed toward the desired blood vessel in such a manner that the guide wire is inserted into that vessel. Thereafter, the catheter is pushed further so as to follow-up the guide wire. In a case where it is difficult to insert the catheter along the guide wire, the base end of the catheter is rotated in clockwise or counterclockwise direction and the catheter is being pushed and inserted further under the rotating condition until it reaches at the selected blood vessels. Since the tip portion of the catheter according to the present invention has sufficient flexibility, it can be passed through or inserted into blood vessels in the brain having a network of narrow and complicated blood vessels. Further, when it is passed through bent portions or curved portions of blood vessels, the catheter can be easily advanced along the guide wire without kinking since the catheter is provided with the coil layer at the tip portion thereof.

Then, the guide wire is removed, and then an X-ray image forming agent is injected from the up-stream side of the cerebral aneurysm of the blood vessel through the lumen of the catheter. In this state, the presence of the cerebral aneurysm is confirmed under the X-ray inspection.

Thereafter, the catheter is further advanced. When the catheter reaches at the desired position, the distal end portion is inserted into and put at the region of the cerebral aneurysm, and at this time, liquid-type thrombus agents or tiny coils are introduced thereinto. When this introduction operation is complete, the catheter is withdrawn from the blood vessel.

Other objects, structures and functions of the present invention will become more apparent from the following description of the invention and the description of the preferred embodiments when taking in conjunction with the appended drawings.

DETAILED DESCRIPTION OF THE PREFERRED EMBODIMENTS

With reference to the drawings, a detailed description of the embodiments of a catheter according to the present invention will now be given below.

Figure 1:
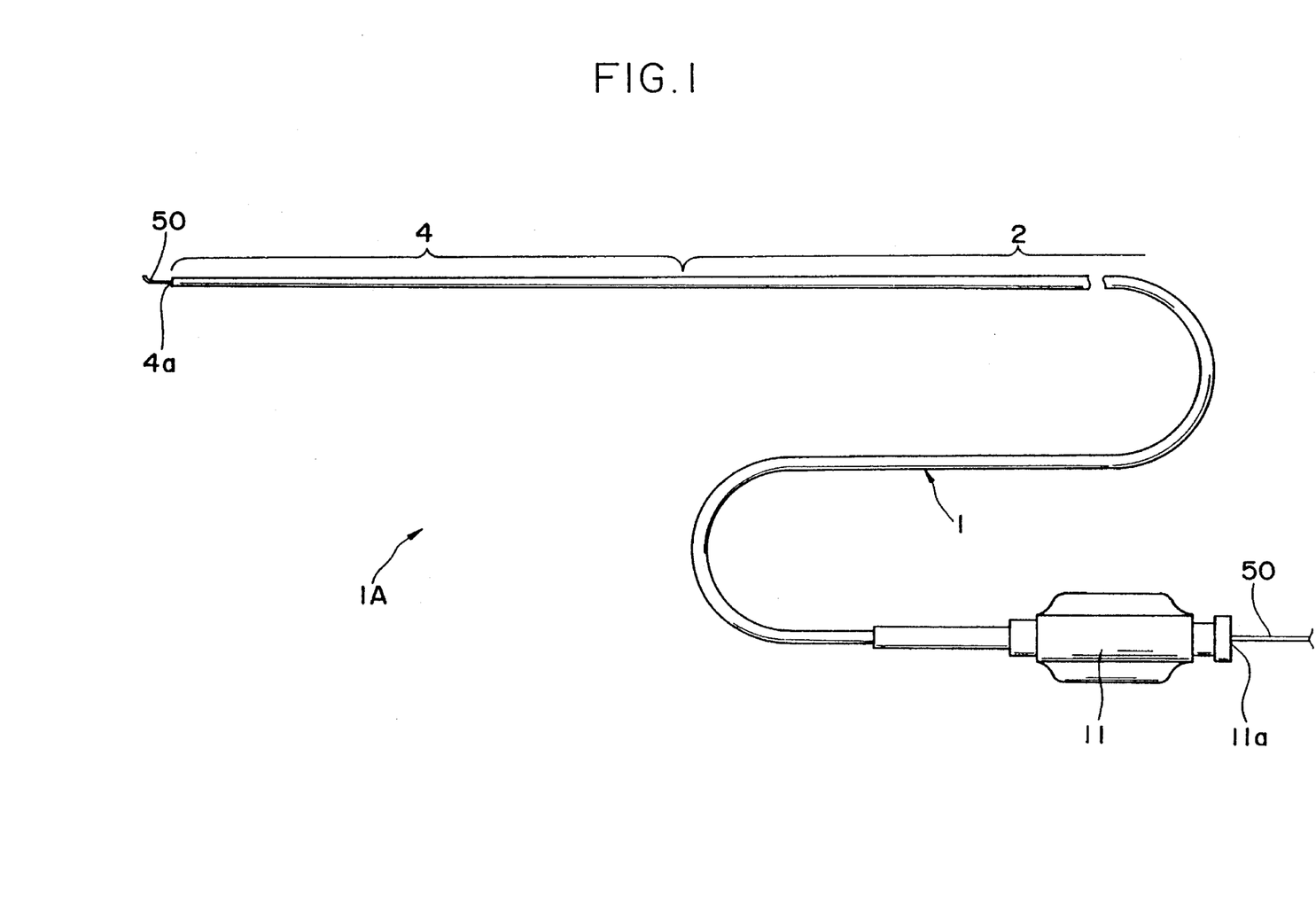
FIG. 1 is an overall view of a catheter instrument according to the present invention.

FIG. 1 is an overall view of a catheter instrument according to a first embodiment of the present invention. As shown in FIG. 1, a catheter instrument 1A comprises a catheter 1, which is made up of a main body portion 2 and a tip portion 4, and a hub 11 provided at the proximal end of the catheter 1. The tip portion 4 has an opening 4a at a distal end thereof, which communicates with a lumen that runs from the opening 4a to a base portion 11a of the hub 11. Also, a guide wire 50 is passed through the lumen so that a tip portion of the wire 50 protrudes out of the opening 4a. in this embodiment, the total length of the catheter is roughly 1500 mm, the length of the tip portion 4 is roughly 200 mm, and the length of the main body portion 2 is roughly 1300 mm.

Figure 2:
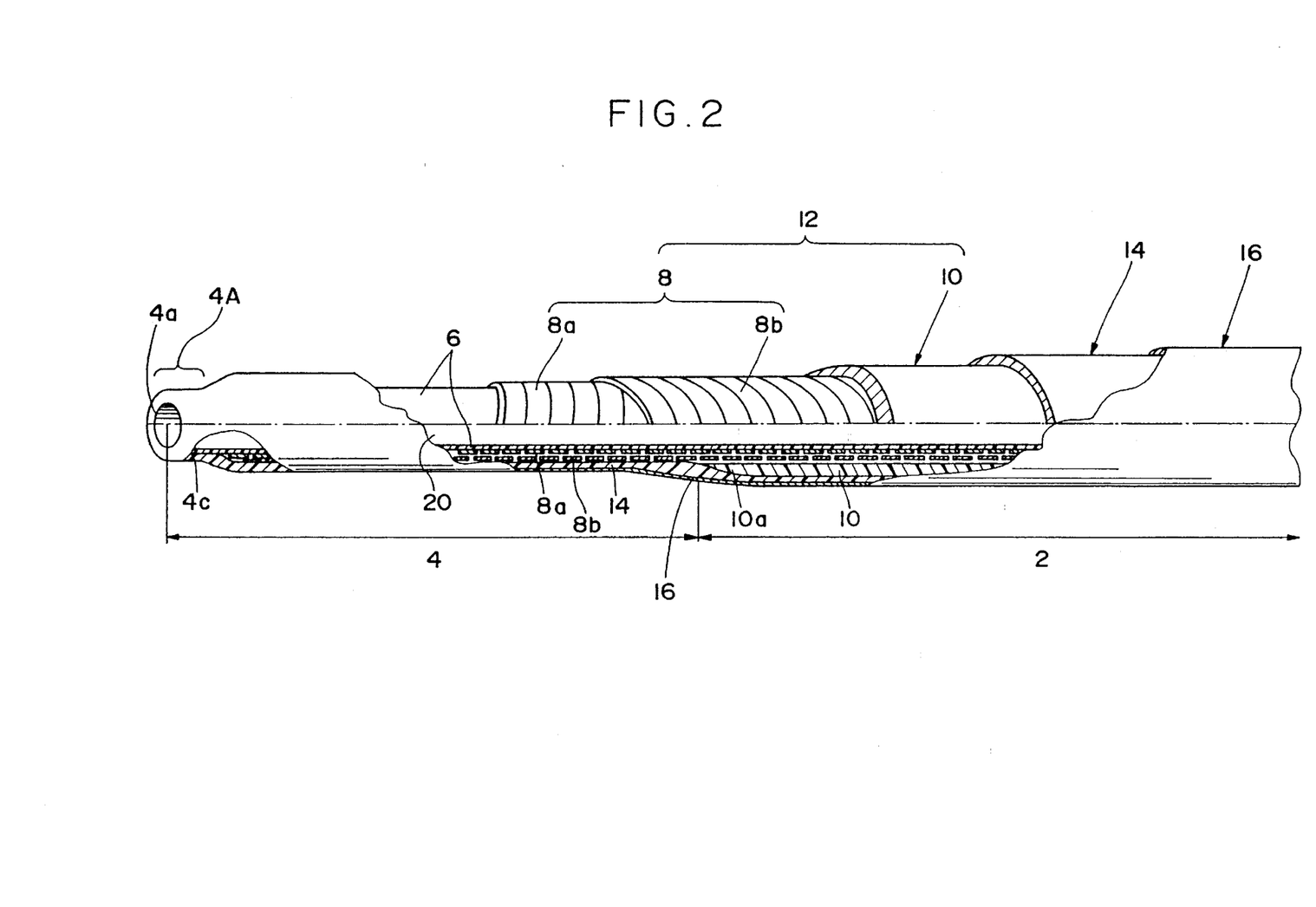
FIG. 2 is a partially cut-away perspective view of a first embodiment of a catheter according to the present invention.

FIG. 2 is an enlarged cut-away view of a distal side (the left side of FIG. 1) of the catheter 1 shown in FIG. 1. As shown in FIG. 2, the main body portion 2 of the catheter is made up of a relatively flexible inner layer 6, an intermediate layer 12 formed around the outside of the inner layer 6 and comprised of a coil layer 8 and a rigid layer 10 having a relatively high rigidity, and a relatively flexible outer layer 14 formed around the intermediate layer 12. The tip portion 4 of the catheter 1 is made up of the inner layer 6, the coil layer 8 and the outer layer 14.

Provided on the outer surface of the outer layer 14 is a hydrophilic lubrication layer 16 having hydrophilic properties. The hydrophilic lubrication layer 16 serves so as to improve the slidability of the catheter 1 within guiding catheters, blood vessels and the like due to the given hydrophilic properties. Furthermore, it is preferred that the hydrophilic lubrication layer 16 be coated with an anticoagulating agent such as heparin solution or the like. Moreover, it is also preferred that such an anticoagulating or anti-thrombogenic agent is added to the lubrication layer 16. In this way, it is possible to improve the anti-thrombogenic properties of the catheter 1.

The inner layer 6 is provided so as to run the entire length of the catheter 1, and the lumen 20 is formed inside the inner layer 6 so as to run from the opening 4a to the base portion 11a of the hub 11. The inner layer 6 is formed from a tube-shaped member having flexibility characteristics that allow it to follow-up the bent portions of a blood vessel, into which the catheter 1 is inserted, without giving any adverse effects on the blood vessel. The inner diameter and outer diameter of the inner layer 6 are roughly uniform to allow easy passage of a guide wire 50 and easy supply of medications and thrombus agents or member. As the materials for constructing the inner layer 6, it is preferable to use a material having excellent chemical resistance properties which are not affected by the medicines to be supplied through the lumen. In particular, in the case of the catheter for use in embolectomy procedures, it is also preferable to have solvent resistance properties in addition to the chemical resistance properties, because there is the case that the thrombus agents includes a solvent such as DMSO, ethanol or cyanoaclylate or the like. Further, it is also preferable that the inner layer is formed from the material with which the inner surface of the inner layer can be formed into a low frictional smooth surface, in order to improve slidability at the time when the guide wire or the like is passed through the lumen 50 or in order to make easy the passage of the thrombus agent which is formed from a tiny coil. For these reasons, as the material for forming the inner layer 6, materials which have flexibility and chemical resistance properties and slidability are used. Example of such a material includes soft fluoro-based resins, fluoro-based elastomer.

In the main body portion 2 of the catheter 1, the intermediate layer 12 is formed from the rigid layer 10 and the coil layer 8, and in the tip portion 4 of the catheter 1, the intermediate layer 12 is formed from the coil layer 8. The intermediate layer 12 is provided around the outside of the inner layer 6 and inside the outer layer 14 of which structure will be described later. The rigid layer 10 is provided around the outside of the coil layer 8. The distal end and proximal end of the middle layer 12 are bonded to the outer layer 14 and/or the inner layer 6. In this way, it is possible for the catheter 1 to have excellent torque transmission ability, pushability and pressure resistance characteristics.

The rigid layer 10 is formed from a tube having a relatively high rigidly. This rigid layer 10 is provided so as to improve the rigidity of the catheter 1 and therefore to improve the pushability for transmitting pushing force applied at the proximal end of the catheter to the tip portion 4 of the catheter. As for the thickness of the rigid layer 10, it is roughly fixed over the axial direction thereof, but at a tip section 10a the thickness gradually becomes narrow. Thus, with this construction, it is possible to more effectively prevent the catheter from kinking. In this connection, polyimide is the preferred material used for constructing the rigid layer 10. With this result, the main body portion 2 having such a rigid layer 10 can have an excellent pushability.

The coil layer 8 is provided along the entire length of both the main body portion 2 and the tip portion 4. The coil layer 8 is provided in order to impart excellent torque transmission ability and anti-kink characteristics to the catheter 1. Further, at the same time the coil layer 8 improves the pushability of the catheter 1. Furthermore, since the coil layer 8 is provided on the area from near the tip section 10a of the rigid layer 10 to the distal side therefrom (left side of FIG. 2), it is possible to prevent kinks from being caused at the section where a difference in rigidity is established due to presence or not presence of the rigid layer 10. In particular, the coil layer 8 is constructed from two coils (double coils) wound or wrapped in opposite directions relative to each other over the entire length thereof. Namely, these two coils are composed of an inner coil 8a and an outer coil 8b both formed from a flat coil wire. For example, when the coil wire of the inner coil 8a is wound in the clockwise direction, the coil wire of the outer coil 8b is wound in the counter-clockwise direction. The coil wires of both the inner coil 8a and the outer coil 8b have roughly flat, rectangular cross sections and have a pitch of 0.12 mm and a coil spacing of 0.02 mm. Both the coil wire of the inner coil 8a and the coil wire of the outer coil 8b are wound in opposite directions so as to have an angle of approximately 80 degree with respect to the axial direction of the catheter 1. Also, both the coil wires of the inner coil 8a and the outer coil 8b have a thickness of about 0.01 mm and are constructed from a metal such as stainless steel (SUS304).

By constructing the coil layer 8 from the two coils wound in opposite directions as described above, it is possible to obtain an excellent torque transmission ability when an operator turns the catheter 1 by operating its proximal end irrespective of the rotational direction (clockwise or counterclockwise). Furthermore, compared to a one coil (single coil) structure, the two coil structure can have more excellent anti-kink characteristics and is far more efficient for preventing the lumen from being pressed.

The outer layer 14 is constructed from a relatively flexible tube-shaped element. The outer layer 14 can be formed easily by adhering a heat shrinkable tube which is shrunk when heated to the surface of the inner layer 6 or the intermediate layer 12 and then by causing thus adhered heat shrinkable tube to be shrunk by applying heat. Such a heat shrinkable tube is preferably formed of for example a polyolefine type of resin. According to the outer layer having the above structure, since it is possible to fix the intermediate layer 12 in place by suppressing bulging and loosening of the outer coil 8b, the torque transmission ability and pushability of the catheter are further improved. It is also possible to construct the outer layer 14 from denatured polyolefine.

Provided on the outer surface of the outer layer 14 is the hydrophilic lubrication layer 16 which runs the entire length of the catheter 1. The lubrication layer 16 is fixed to the outer surface of the outer layer 14 under the bonding force to the extent of being able to bear practical use. The lubrication layer 16 exhibits its lubrication characteristics when it comes into contact with water. By providing such a lubrication layer 16, when the catheter 1 is inserted into a lumen of a guiding catheter or a blood vessel, and in particular when the catheter 1 is selectively inserted into one of branches of blood vessels having an acute angle or when the catheter 1 is inserted into curved or bent portions of distal blood vessels, it is possible to reduce the frictional resistance between inside surfaces such blood vessel and the outside surface of the catheter 1. Thus, it becomes possible to transmit the rotational force or pushing force added to the proximal end of the catheter by an operator to the tip portion 4 of the catheter 1 as they are (without losses), thus resulting in easy, reliable and safe insertion of the catheter 1.

As for the preferred material for constructing the hydrophilic lubrication layer 16, it is selected depending on the material of the outer layer 14. When the outer layer 14 is formed of denaturated polyolefine, a block-copolymer formed by a hydrophilic compound block and a hydrophobic compound block is preferably used. Example of such a block-copolymer includes a block-copolymer of polyglycidyl-methacrylate (PGMA) and dimethyl-acrylicamide (DMAA). The hydrophilic compound of the block-copolymer is excellence in lubrication properties since it is a water-swelling compound, and it can also exhibit anti-thrombogenic properties due to its micro-domain structure between the hydrophilic section and the hydrophobic section.

Provided at the distal side of the tip portion 4 is a distal end portion 4A which forms the most flexible part of the entire catheter body. The distal end portion 4A is constructed from the inner layer 6 and the outer layer 14 and includes the opening 4a which communicates with the lumen 20. The length of the distal end portion 4A along the axial direction of the catheter 1 is approximately 1.0 mm–3.0 mm. By providing the catheter 1 with the distal end portion 4A, it is possible to reduce the risk of injury to very delicate blood vessel membranes, and furthermore improves the ability of the catheter 1 to follow-up the curved portions and bent portions within a blood vessel or guiding catheters.

Provided on the distal end portion 4A is a ring-shaped or coil-shaped X-ray image forming element 4C made from gold or white gold, for example. By providing the distal end portion 4A with the X-ray image forming element 4C, it becomes possible to use X-ray images to accurately confirm the position of the distal end portion 4A of the catheter 1 within a living body.

As for the outer diameter of the catheter 1, the main body portion 2 has the largest outer diameter, the distal end portion 4A has the smallest outer diameter, and the tip portion 4 has an outer diameter that lies somewhere therebetween. In one preferred example, the outer diameter of the main body portion 2 is approximately 0.92 mm, the outer diameter of the tip portion 4 is approximately 0.80 mm, and the outer diameter of the distal end portion 4A is approximately 0.72 mm.

Now, the second embodiment of a catheter instrument according to the present invention is basically the same as the first embodiment shown in FIG. 1. Therefore, the catheter instrument is comprised of a catheter 1 having a main body portion 2 and a tip portion 4 and a hub 11 provided at the proximal end of the catheter 1. The tip portion 4 has an opening 4a which communicates with a lumen that runs from the opening 4a to a base portion 11a of the the hub 11.

Figure 3:
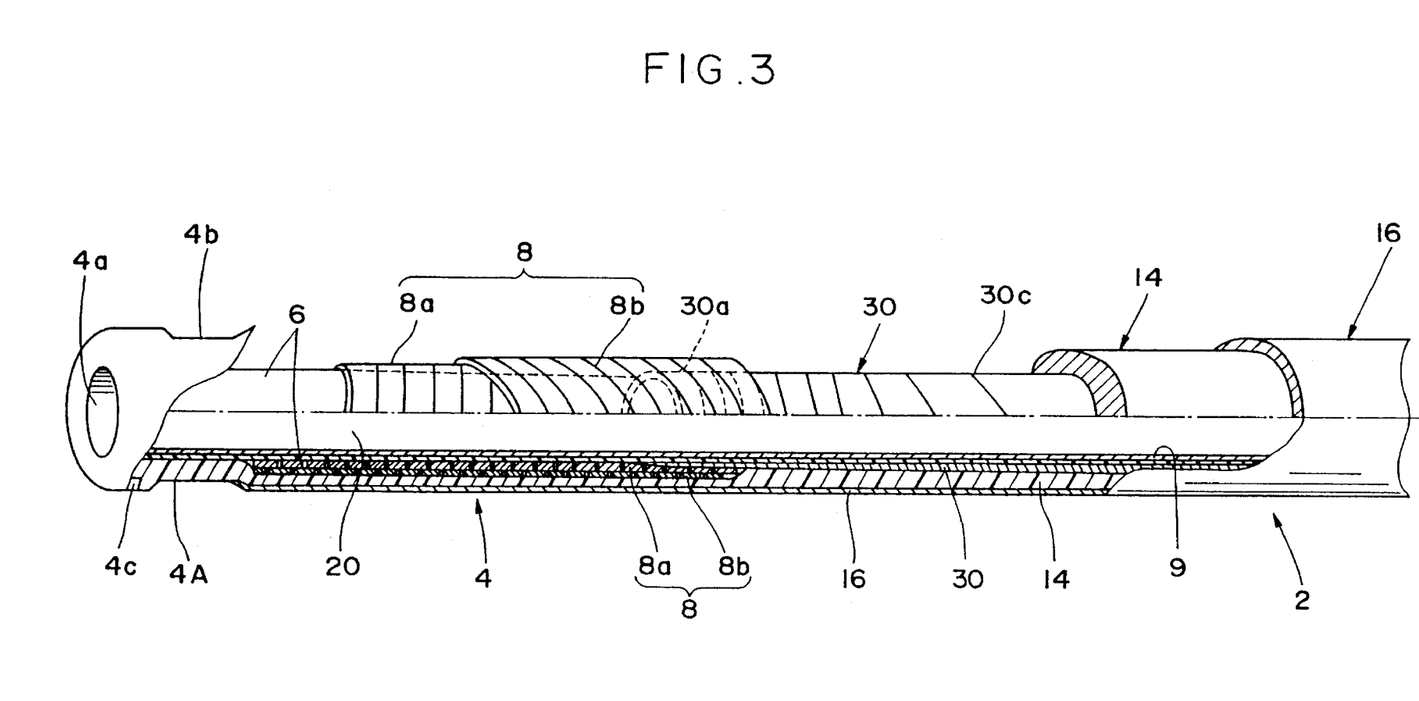
FIG. 3 is a partially cut-away perspective view of a second embodiment of a catheter according to the present invention.

FIG. 3 is an enlarged cut-away view of a distal side (the left side of FIG. 1) of the second embodiment of the catheter 1 according to the present invention. As shown in FIG. 3, the catheter 1 is composed of a main body portion 2, a tip portion 4 and a distal end portion 4A. The main body portion 2 is constructed from a relatively flexible inner layer 6, a metal tube layer 30 which is provided around the inner layer 6 to act as a rigid layer, a coil layer 8 which extends from the vicinity of a tip portion 30a of the metal tube layer 30 towards the distal end of the catheter 1, and a relatively flexible outer layer 14. The tip portion 4 is constructed from the inner layer 6 which extends from the main body portion 2, the coil layer 8, and the outer layer 14 which extends from the main body portion 2. The distal end portion 4A is constructed from the inner layer 6 and the outer layer 14 which extend from the tip portion 4. In this embodiment having the above constructions, the metal tube layer 30 and the coil layer 8 form an intermediate layer that is positioned between the inner layer 6 and the outer layer 14.

The relatively flexible inner layer 6 is a tube-shaped element that is provided so as to run roughly the entire length of the catheter and includes a lumen 20 through which guide wires, medicines, thrombus agents or member and the like are passed. The diameter of the lumen, or more specifically stated, the inner diameter of the inner layer 6 is roughly the same from the main body portion 2 to the tip portion 4 thereof in order to make it easy for inserted things to be passed therethrough. For constructing the inner layer 6 of the second embodiment, it is possible to use the same construction materials described above with reference to the first embodiment. Furthermore, a hydrophilic lubrication layer 9 is provided on the inner surface of the lumen 20 in the same manner as the first embodiment.

The metal tube layer 30 which forms a rigid layer has a relatively higher rigidity than that of the outer layer 14, and this results in the catheter having improved rigidity in the axial, radial and circumferential directions thereof, which in turn improves the pushability and torque transmission characteristics of the catheter. Furthermore, since the metal tube layer 30 has a wide degree of elasticity, it will experience little or no plasticized deformation even when bending stress is applied during the normal use. Except for the tip portion 30a of the metal tube layer 30 which has a relatively thin thickness, the remaining portion of the metal tube layer 30 has roughly the same thickness along the axial direction of the catheter.

Furthermore, a spiral-shaped slit 30c is provided in the vicinity of the tip portion 30a of the metal tube layer 30. This spiral-shaped slit 30c is provided in a section of the metal tube layer 30 that is roughly 150 mm long with respect to the axial direction or the catheter. As for the pitch of the spiral-shaped slit 30c, it is made to gradually decrease in the direction toward the tip portion 30a (towards the left side in FIG. 3) so as to gradually lower the rigidity of the metal tube layer 30 in the same direction, and this makes it possible to effectively prevent the catheter from kinking. The metal tube layer 30 is made, for example, from a stainless steel pipe (SUS304). It is to be noted here that it is possible to use a construction other than the metal tube layer 30 for forming a rigid layer. For example, it is possible to use a metal layer comprised of a mesh or braid or the like formed from metal wires instead of the metal tube layer 30.

The coil layer 8 is provided in order to achieve the same purpose of that of the above-described embodiment. This coil layer 8 has its base positioned in the vicinity of the tip portion 30a of the metal layer 30 and extends over the tip portion 4. By providing the coil layer 8 such that its base is positioned in the vicinity of the tip portion 30a of the metal tube layer 30 and it extends over the tip portion 4 as described above, the coil layer 8 can loosen difference in the rigidity between at a portion where the metal tube layer 80 is provided and at a portion where no metal tube layer is provided to dissipate concentration of stress over such region, thereby enabling to improve kinking preventing effects. Therefore, there will not be a case that a guide wire can not be advanced or retracted due to a kinking of the catheter when the guide wire 50 is inserted into the lumen 20 of the catheter.

The coil layer 8 is constructed in the same manner as described above with reference to the first embodiment. Namely, the coil layer 8s is formed from a double layer coil which is constructed from an inner coil 8a, which is wound in one direction, and an outer coil 8b, which is wound in the opposite direction. The cross-sectional shape, dimensions and construction materials of the inner coil 8a and outer coil 8b are the same as or similar to those for the inner and outer coils of the first embodiment described above and therefore the use and effects achieved by the double layer coil are also the same as those described with reference to the first embodiment.

The region of overlap of the coil layer 8 and the tip portion 30a of the metal tube layer 30 is approximately 2 mm in length with respect to the axial direction of the catheter. In order to prevent a large bulging in the catheter at the region of overlap, it is possible to reduce the thickness of the metal tube layer 30 and the coil layer 8 at that place where they overlap with each other, or it is also possible to shift the base end of the inner coil 8a towards the tip of the catheter and then position the base end of the outer coil 8b at a place between the tip of the metal tube layer 30 and the base end of the inner coil 8a. Furthermore, it is preferred that the length of the region of overlap between the coil layer 8 and the metal tube layer 30 be less than ⅓ the total length of the portion of the metal tube layer 30 in which the spiral-shaped slit 30c is provided.

The outer layer 14 is constructed from a relatively flexible tube-shaped member. In the same manner as was described above with reference to the first embodiment, a hydrophilic lubrication layer 16 is provided on the outer surface of the outer layer 14. This hydrophilic lubrication layer 16 perform functions and exhibit effects which are the same as those described above with reference to the lubrication layer of the first embodiment.

Further, in the same manner as was described above with reference to the first embodiment, the distal end portion 4A provided at the distal side of the tip portion 4 is constructed from the inner layer 6 and the outer layer 14 and has an opening 4a which communicates with the lumen 20. The distal end portion 4A also includes a constricted portion 4b spaced a slight distance away from the opening 4a and having a reduced outer diameter relative to the rest of the distal end portion 4A. As the constricted portion 4b is the most flexible portion of the distal end portion 4A, is possible to easily change the direction of the distal end portion 4A, and this enables the catheter to follow more easily the bent portions and branches of blood vessels and the like. And in the same manner as described above for the first embodiment, the distal end portion 4A is provided with an X-ray image forming element 4c.

Figure 4:
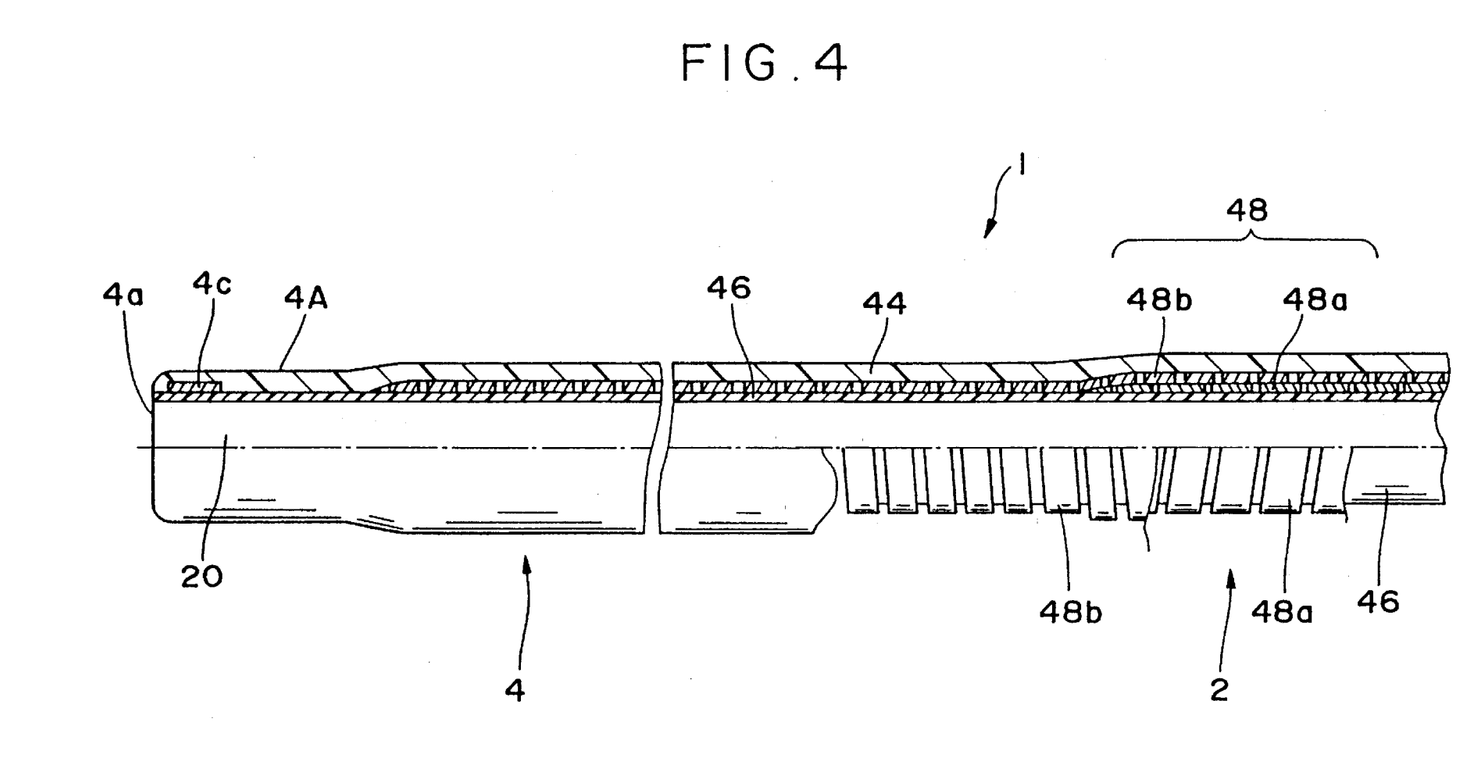
FIG. 4 is a partially cut-away side view of a third embodiment of a catheter according to the present invention.

FIG. 4 is a partial cut-away view of a third embodiment of a catheter according to the present invention. In this embodiment, a catheter 1 includes a main body portion 2 and a tip portion 4 and is constructed from an inner layer 46 that runs roughly the entire length of the catheter 1, a coil layer 48 that forms an intermediate layer, and an outer layer 44. The coil layer 48 is constructed from a relatively rigid first coil 48a and a relatively flexible second coil 48b.

Formed in the inner layer 46 is a lumen 20 which enable guide wires, medicines and the like to be passed through the catheter 1. The lumen 20 has roughly the same diameter throughout the main body portion 2 and the tip portion 4 of the catheter 1. Also, in the same manner as was described above with reference to the second embodiment, the inner surface of the lumen 20 is provided with a hydrophilic lubrication layer (not shown in the drawings). The thickness of the inner layer 46 is roughly the same throughout the main body portion 2 and the tip portion 4. Also, the construction material of the inner layer 46 is the same throughout the main body portion 2 and the tip portion 4 and is selected from the same materials described previously above.

In the main body portion 2, the relatively rigid first coil 48a is wound around the inner layer 46. The first coil 48a is a flat type of metal coil made from a stainless steel wire or the like and has a base end pitch of approximately 0.12 mm and a coil spacing of approximately 0.02 mm. The flat coil wire has a cross-sectional rectangular shape with a vertical length (i.e., thickness) of approximately 0.01 mm and a horizontal length (i.e., coil width) of approximately 0.1 mm. By providing the first coil 48a having the above structure, it becomes possible to impart a sufficient rigidity to the main body portion 2. The first coil 48a terminates at an intermediate place along side of the catheter 1. At the distal side of the first coil 48a, the pitch of the coil is smaller relative to the pitch at the proximal side thereof in order to gradually change the rigidity of the first coil 48a.

Provided around the outside of the first coil 48a is the second coil 48b. In this arrangement, the rigidity of the outside second coil 48b is smaller than the inside first coil 48a. In this regard, it should be noted that there are many ways to provide first and second coils having different rigidities as described above. These ways includes for example first to fourth ways which are described below. Namely, in the first way, one coil is formed from a relatively soft construction material, and the other coil is formed from a relatively hard construction material. In the second way, a coil pitch of one coil is larger than that of the other coil in order to improve rigidity. In the third way, the thickness of one coil is larger than that of the other coil in order to improve rigidity. In the forth way, one coil is formed from a flat coil which can impart relatively high rigidity and the other coil is formed from a coil having a semi-circular cross section which is relatively flexible. Further, it is of course possible to adopt other way which can be obtained from combination of any two more ways selected from the ways mentioned above.

As described in the previous embodiments, the first coil 48a and the second coil 48b are wound in opposite directions. In this case, the second coil 48b extends over the tip end of the first coil 48a and terminates at the tip portion 4. Since the second coil 48b provided in the tip portion 4 is formed from relatively sort material, the catheter having such tip portion can have an improved ability to follow a guide wire when the catheter is inserted into bent blood vessels or put therein, or when selection is made for the advancing direction at blood vessel branches having sharp angles. Further, there is no risk of the lumen being damaged. In this case it is also possible to set the pitch of the second coil 48b at the distal side of the tip portion 4 to be smaller than the pitch of the second coil 48b at the proximal side thereof.

In the present embodiment, the second coil 48b was constructed from the same construction material over its entire length. However, it is possible to arrange a different coil members in the axial direction of the catheter. For example, in order to prevent kinking from being caused in the distal side of the first coil 48a, the rigidity of the second coil 48b is set so as to have the same or less rigidity than that of the first coil 48a, and thus formed second coil 48b is extended into the tip portion 4 over the tip end of the first coil 48a. Further, a relatively flexible another coil member is joined to the tip end of the second coil 48b. In this way, it is possible to prevent kinking from being caused in the vicinity of the tip end of the first coil 48a and at the same time ensure a proper flexibility for the tip portion 4.

Now, in the embodiment shown in FIG. 4, the first coil 48a is provided inside the second coil 48b. However, it is also possible reverse the arrangement such that the relatively hard first coil 48a is provided outside the relatively soft second coil 48b. Also, even though it is not shown in the drawings, it is also possible for the coil layer 48 to include a third coil. In the case where the third coil is provided, it is preferred that the position of the tip end of the third coil in the axial direction of the catheter be arranged to lie between the tip end of the first coil 48a and the tip end of the second coil 48b or at a position located slightly before the tip end of the first coil 48a. In this way, it is possible for the catheter to have multiple sections of different rigidity.

The outer layer 44 is formed around the outer circumference of the coil layer 48 and is fixedly adhered thereto so as not to deteriorate the flexibility of the first and second coils which would be caused by the deformation of these coils. The thickness of the outer layer 44 is roughly the same throughout the entire length of the catheter. As for the outer diameter of the outer layer 44, it is greatest at the place of overlap of the first coil 48a and the second coil 48b, is smaller at the portion where only the second coil 48b exists, and is smallest at the distal end portion 4A. The outer layer 44 is constructed from a relatively flexible material, and the outside surface of the outer layer 44 is coated with a hydrophilic lubrication layer (not shown in FIG. 4) formed thereon, as described above with reference to the previous embodiments. Furthermore, the hydrophilic lubrication layer may contain an anti-coagulating agent therein. Moreover, it is also possible to form an additional coating layer having anti-coagulating property onto the lubrication layer.

As described for the previous embodiments above, a distal end portion 4A is formed at the tip of the tip portion 4. The distal end portion 4A is formed from the inner layer 46 and the outer layer 44 in the same manner as the above described embodiments. In this case, the distal end portion 4A does not include the coil layer 48. Further, as was also described above with reference to the previous embodiments, an X-ray image forming element 4c is provided on the distal end portion 4A to enable the position of the distal end portion 4A to be accurately confirmed by X-ray inspection.

Figure 5:
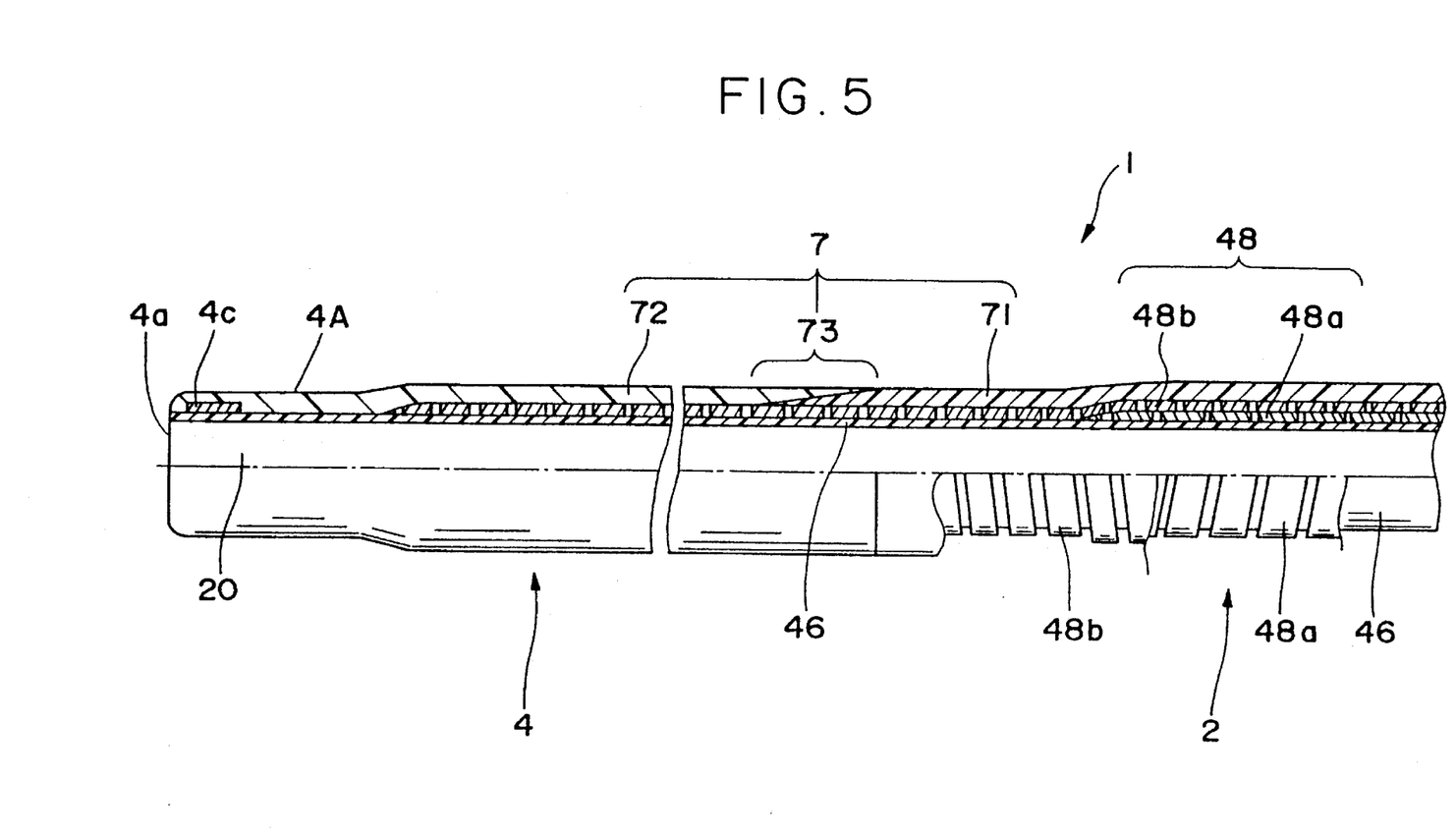
FIG. 5 is a partially cut-away side view of a fourth embodiment of a catheter according to the present invention.

FIG. 5 shows a partially cut-away side view of a catheter according to a fourth embodiment of the present invention. With the exception of an outer layer 7 having a different construction, the catheter 1 shown in FIG. 5 has the same construction as the third embodiment shown in FIG. 4. In this embodiment, the outer layer 7 of the catheter 1 has a relatively rigid first region 71 provided at the proximal side of the catheter 1, a relatively flexible second region 72 that runs from the first region 71 towards the tip of the catheter 1, and a connection portion 73 that connects the first region 71 and the second region 72. The outer layer 7 is provided around the outer surface of the coil layer 48 and is adhered thereto.

The outer diameter of the first region 71 gradually decreases at the distal side thereof so as to form a tapered portion. The second region 72 is fused onto the tapered portion so as to cover the outer surface of that tapered portion, thereby forming the connection portion 73. In this embodiment, the connection portion 73 is positioned on the tip portion 4 of the catheter 1. The thickness and outer diameter of the outer layer 7 at the connection portion 73 is the same as the thickness and outer diameter of the first region 71 and second region 72. The relatively rigid first region 71 is mainly provided on the main body portion 2 of the catheter 1 in order to impart rigidity to the main body portion 2, which in turn makes it easy to push the catheter 1. On the other hand, the relatively flexible second region 72 is provided on the distal side of the catheter 1 in order to ensure flexibility characteristics for the tip portion 4, which in turn exhibits excellent follow-up ability to a guide wire when the catheter is inserted into the bent portions of blood vessels or branches of blood vessel having sharp angles.

The connection portion 73 has a rigidity that lies between the rigidity of the first region 71 and the rigidity of the second region 72. Namely, since the connection portion 73 is constructed from the relatively rigid material of the first region 71 and the relatively flexible material of the second region 72, the ratio containing the relatively hard material and the relatively soft material gradually changes in the axial direction thereof. With this construction, the rigidity of the catheter slowly changes over the connection portion 73 and in the vicinity of the ends thereof, thus making it possible to dramatically improve the anti-kinking effectiveness of the catheter 1. Moreover, since the coil layer 48 is provided under the outer layer 7 so as to extend from the first region 71 through the second region 72, the catheter 1 is even more effective at preventing kinks.

Figure 6:
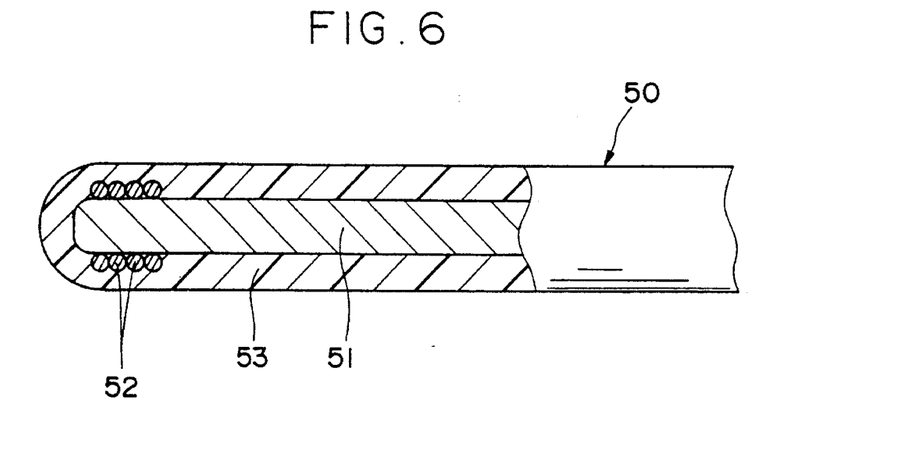
FIG. 6 is a partially cut-away side view of a guide wire used in association with the catheter according to the present invention.

FIG. 6 is a partially cut-away view of an example construction of a guide wire used with the catheter according to the present invention. As shown in FIG. 6, the guide wire 50 is adapted to be passed through the lumen 20 of the catheter 1. The guide wire 50 is constructed from a metal core 51, a coil-shaped X-ray image forming element 52 provided at the tip of the metal core 51, and a cover layer 53 which covers the outer surface of the metal core 51. The core 51 is an elastic element which is constructed, for example, from a metal such as stainless steel, Ni-Ti alloy, piano wire, tungsten wire, or the like. The X-ray image forming member 52 is constructed, for example, from a metal such as gold, white gold or the like. In order to have good slidability with the lumen 20 of the catheter 1, the cover layer 53 is constructed from a material having a low frictional resistance, such as a fluorine based resin. Furthermore, since the cover layer 53 also covers the end surfaces of the core 51 in addition to covering the circumferential surfaces thereof, it becomes possible to prevent injury to the blood vessel membrane when contact occurs between the blood vessel membrane and the guide wire 50.

Figure 7:
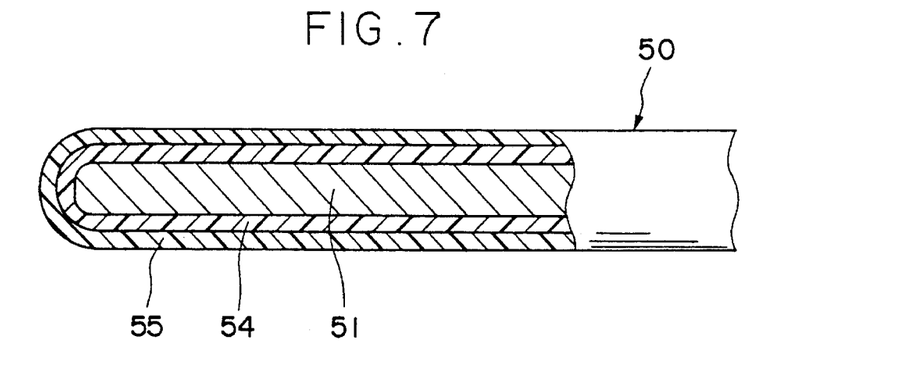
FIG. 7 is a partially cut-away side view which shows a modification of the guide wire used in the catheter according to the present invention.

FIG. 7 is a partial cut-away view of another example construction of a guide wire used with the catheter according to the present invention. As shown in FIG. 7, the guide wire 50 is adapted to be passed through the lumen 20 of the catheter 1. In the same manner as the above-described embodiment, the guide wire 50 is constructed from a metal core 51, a plastic coating layer 54 which covers the outer surface of the metal core 51, and a hydrophilic lubrication layer 55 which is applied to the outer surface of the coating layer 54. Examples of the coating layer 54 include, for example, polyurethane elastomer, polyamide elastomer, denaturated polyolefine and the like. Furthermore, as the cover layer 53 also covers the end surfaces of the core 51 in addition to covering the circumferential surfaces thereof, it becomes possible to prevent injury to the blood vessel membrane when contact occurs between the guide wire 50 and the blood vessel membrane. As for the hydrophilic lubrication layer 55, it may be formed in the same manner as the hydrophilic lubrication layer of the catheter 1 described above.

The guide wires 50 shown in FIG. 6 and FIG. 7 have diameters that enable them to be passed with ease and good slidability through the lumen 20 of the catheter 1. For example, the diameters are set to the size which lies between 0.010 inch and 0.025 inch.

Figure 8:
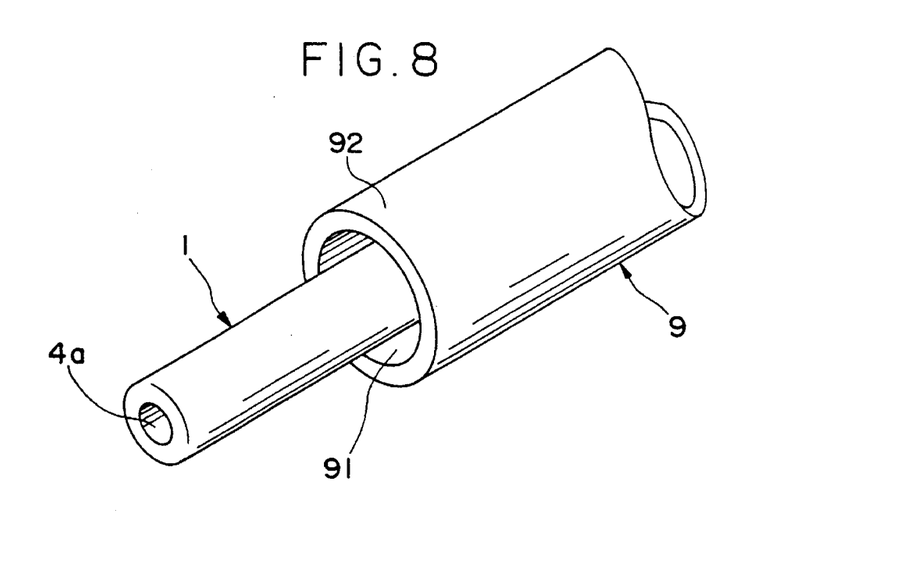
FIG. 8 is a perspective view which shows a structure example of a guiding catheter according to the present invention.

FIG. 8 is a perspective view of an example construction of a guiding catheter. As shown in FIG. 8, a guiding catheter 9 is comprised of a tube-shaped body having a lumen 91 through which the catheter 1 is passed. In constructing such a guiding catheter 9, it is possible to use, for example, polyurethane elastomer, polyamide elastomer, and polymer alloy containing polyamide. As for the inner diameter of the guiding catheter 9, it is set so as to enable the catheter 1 to be passed with ease and good slidability through the lumen 91 thereof. For example, it is set to the size which lies between 1.00 mm and 1.80 mm. The outer diameter and wall thickness of the guiding catheter 9 are roughly uniform over the entire length of the guiding catheter 9, but it is also possible to provide a tapered portion of gradually reducing diameter in the vicinity of the tip portion 92 of the guiding catheter 9.

Furthermore, it is preferred that a hydrophilic lubrication layer (not shown in the drawings) be provided on the outer surface of the guiding catheter 9 and/or the inner surface of the lumen 91 of the guiding catheter 9. In this way, it is possible to improve both the slidability of the guiding catheter 9 when it is inserted into a blood vessel or the like and the slidability of the catheter 1 when it is inserted into the lumen 91 of the guiding catheter 9.

As stated in the foregoings, the catheter according to the present invention has excellent operability, and in particular it is excellent in slidability, anti-kinking characteristics and torque transmission ability. Further, the catheter also has improved pushability and anti-chemical resistance. Therefore, the catheter can perform delicate operations easily even when it is inserted into narrow and complicated network of blood vessels for carrying out treatment for blood vessels of the brain. As a result, it is possible to shorten the time required in carrying out the treatment, and the risk to injury the blood vessels can be reduced.

Finally, it should be noted that the present invention is no limited to the embodiments described above. The scope of the present invention will be determined only by the following claims.

What is claimed is:

1. A catheter, comprising:

an inner layer;

an outer layer; and an intermediate layer arranged between said inner and outer layers, said intermediate layer including a coil layer having a double layer coil portion composed of an inner coil wound in a first direction and an outer coil wound around the outside of said inner coil in a second direction that is opposite to said first direction, wherein said inner coil and said outer coil are formed from flat members whose ratios of thickness to width of cross section are less than 1.

2. The catheter as claimed in claim 1, wherein said coil layer has a first portion having a relatively high rigidity and a second portion having a rigidity less than that of said first portion, and said second portion is positioned at the distal side of said catheter than the position of said first portion.

3. The catheter as claimed in claim 1, wherein said double coil layer portion has a tip end, and said coil layer further includes a single coil layer coupled to the tip end of said double layer coil portion, and said single coil layer is formed from either of said inner or outer coil.

4. The catheter as claimed in claim 3, wherein the rigidity of said inner coil is different from that of said outer coil.

5. The catheter as claimed in claim 1, wherein said coil layer is arranged over a substantially entire length of said catheter.

6. The catheter as claimed in claim 1, wherein said inner layer is arranged over a substantially entire length of said catheter.

7. The catheter as claimed in claim 6, wherein said inner layer has a constant inner diameter along the entire length of said catheter, and said inner layer has an inner surface which defines a lumen and said inner surface is formed into a smooth surface having no step portion.

8. The catheter as claimed in claim 10, wherein said inner surface of said inner layer is formed so as to have a low frictional characteristic and said inner surface has a chemical resistance property.

9. The catheter as claimed in claim 6, wherein said inner layer is formed of at least one material selected from the group consisting of soft fluorine-based resin, low density polyethylene and denaturated polyolefine.

10. The catheter as claimed in claim 1, wherein said outer layer is formed from a heat shrinkable resin which is shrunk when heated.

11. The catheter as claimed in claim 1, further comprising a hydrophilic lubricant layer provided around said inner layer and/or said outer layer.

12. The catheter as claimed in claim 11, wherein said hydrophilic lubricant layer has anti-thrombogenic property.

13. The catheter as claimed in claim 1, wherein said catheter further includes a distal end portion which has the largest flexibility among the portions of said catheter, and said intermediate layer is not arranged in said distal end portion.

14. The catheter as claimed in claim 13, wherein said distal end portion includes X-ray image forming element.

15. The catheter as claimed in claim 1, wherein said catheter is adapted to be inserted for use inside a cerebral blood vessel.

16. The catheter as claimed in claim 15, wherein the outer diameter of said catheter is less than or equal to 1.0 mm.

17. A catheter instrument, comprising:

a catheter including an inner layer; an outer layer; and an intermediate layer arranged between said inner and outer layers, said intermediate layer including a coil layer having a double layer coil portion composed of an inner coil wound in a first direction and an outer coil wound around the outside of said inner coil in a second direction that is opposite to said first direction, wherein said inner coil and said outer coil are formed from flat members whose ratios of thickness to width of cross section are less than 1; and a guide wire which is used by being inserted into a lumen defined by said inner layer of said catheter.

18. The catheter instrument as claimed in claim 17, wherein said guide wire is composed of a core member, an X-ray image forming element provided at a tip portion of said core member, and a coating layer which covers the outer surface of said core member.

19. The catheter instrument as claimed in claim 17, said guide wire is composed of a core member, a coating layer which covers the outer surface of said core member and a hydrophilic lubricant layer fixed onto the outer surface of said coating layer.

20. A catheter instrument, comprising:

a catheter including an inner layer; an outer layer; and an intermediate layer arranged between said inner and outer layers, said intermediate layer including a coil layer having a double layer coil portion composed of an inner coil wound in a first direction and an outer coil wound around the outside of said inner coil in a second direction that is opposite to said first direction, wherein said inner coil and said outer coil are formed from flat members whose ratios of thickness to width of cross section are less than 1;

a guide wire which is used by being inserted into a lumen defined by said inner layer of said catheter; and a guiding catheter having a lumen through which said catheter is inserted.

21. The catheter as claimed in claim 20, wherein said guiding catheter has inner and outer surfaces, and a hydrophilic lubricant layer is arranged onto said inner and/or outer surface.

22. A catheter having a proximal side, comprising:

an inner layer;

an outer layer; and an intermediate layer arranged between said inner and outer layers, said intermediate layer including a coil layer having a double layer coil portion composed of an inner coil wound in a first direction and an outer coil wound around the outside of said inner coil in a second direction that is opposite to said first direction, said inner coil and said outer coil being formed from flat members whose ratios of thickness to width of cross section are less than 1, said outer layer including at the proximal side of said catheter a first region which is relatively rigid, and a second region positioned at a distal side from said first region which is relatively flexible.

23. The catheter as claimed in claim 22, wherein said outer layer has a coupling section disposed between said first and second regions for coupling these regions, and said coupling section has a rigidity between the rigidities of said first and second regions.

24. A catheter, comprising:

an inner layer;

an outer layer; and an intermediate layer arranged between said inner and outer layers, said intermediate layer including a coil layer having a double layer coil portion composed of an inner coil wound in a first direction and an outer coil wound around the outside of said inner coil in a second direction that is opposite to said first direction, wherein said inner coil and said outer coil are formed from flat members whose ratios of thickness to width of cross section are less than 1, said intermediate layer also including a rigid layer having a rigidity greater than the rigidity of at least one of said inner and outer layers.

25. The catheter as claimed in claim 24, wherein said catheter has a main body portion is positioned at a proximal side of said catheter in an axial direction thereof and a tip portion at a distal side of said main body portion, in which said rigid layer is arranged in said main body portion and said coil layer is arranged at least in said tip portion.

26. The catheter as claimed in claim 24, wherein said rigid layer is arranged such that at least a part of said rigid layer overlaps said coil layer.

27. The catheter as claimed in claim 24, wherein said rigid layer has a rigidity reducing means for reducing the rigidity of said rigid layer at a tip side of said rigid layer.

\* \* \* \* \*

UNITED STATES PATENT AND TRADEMARK OFFICE
CERTIFICATE OF CORRECTION

PATENT NO. : 5,554,139
DATED : September 10, 1996
INVENTOR(S) : Naofumi OKAJIMA

It is certified that error appears in the above-indentified patent and that said Letters Patent is hereby corrected as shown below:

In Column 12, line 65, after "catheter" and before "is" insert -- 1 --.

In Column 16, line 64, delete "80" and insert -- 30 --.

In Column 18, line 22, delete "side of".

In Column 18, line 22, after "catheter 1" insert -- and is therefore not present in the distal side of the catheter 1 --.

In Column 18, line 51, delete "sort" and insert -- soft --.

In Column 22, line 19, delete "10" and insert -- 6 --.

Signed and Sealed this

Eighteenth Day of March, 1997

Attest:

BRUCE LEHMAN

Attesting Officer

Commissioner of Patents and Trademarks